United States Patent [19]

Neuberger

[11] Patent Number: 6,165,205
[45] Date of Patent: Dec. 26, 2000

[54] METHOD FOR IMPROVED WOUND HEALING

[75] Inventor: Wolfgang Neuberger, Labaun, Malaysia

[73] Assignee: CeramOptec Industries, Inc., East Long Meadows, Mass.

[21] Appl. No.: 09/113,387

[22] Filed: Jul. 10, 1998

[51] Int. Cl.⁷ .................................................. A61N 5/00
[52] U.S. Cl. ............................................................ 607/89
[58] Field of Search ..................... 606/2, 9, 13; 607/88, 607/89, 90, 92, 93; 602/2, 41–43

[56] References Cited

U.S. PATENT DOCUMENTS

| | | | |
|---|---|---|---|
| 4,905,690 | 3/1990 | Ohshiro et al. | 607/89 |
| 4,930,504 | 6/1990 | Diamantopoulos et al. | 607/88 |
| 5,140,984 | 8/1992 | Dew et al. | 607/89 |
| 5,344,433 | 9/1994 | Talmore | 607/88 |
| 5,474,549 | 12/1995 | Ortiz et al. | 606/9 |
| 5,505,726 | 4/1996 | Meserol | 606/9 |
| 5,616,140 | 4/1997 | Prescott | 606/10 |
| 5,755,752 | 5/1998 | Segal | 607/89 |
| 5,800,479 | 9/1998 | Thiberg | 607/88 |
| 6,063,108 | 5/2000 | Salansky et al. | 607/89 |

OTHER PUBLICATIONS

Lasers Aid In the Destruction Of Bacteria. Photonics Spectra vol. 32 Feb. 1998, p. 45.

*Primary Examiner*—Linda C. M. Dvorak
*Assistant Examiner*—Bryan K. Yarnell
*Attorney, Agent, or Firm*—Bolesh J. Skutnik; B J Associates

[57] ABSTRACT

A laser non-ablative laser method that will accelerate and improve wound healing, particularly in situations where complicating factors are present. In particular, it is believed that the present invention produces selective papillary dermal injury which activates the production of fibroblasts and stimulates the synthesis of collagen to promote wound healing. Additionally, the likelihood of infection at the wound site is reduced by simultaneously employing a transparent wound cover that allows for small molecule permeation, while effectively preventing microbial invasion. To further enhance the healing process, the laser therapy can be preceded by mechanically scraping the surface of the wound to remove necrotic tissue. Additional methods may also be employed after the laser treatment to prevent tissue dehydration, to accelerate angiogenesis, and to increase the breakdown of dead tissue and fibrin.

10 Claims, 4 Drawing Sheets

METHOD FOR IMPROVED WOUND HEALING

BACKGROUND OF THE INVENTION

1. Field of the Invention

The present invention relates to a device and method that will accelerate and improve wound healing, particularly where complicating factors are present that may be associated with metabolic disorders such as diabetes, radiation or chemically treated cancer patients, or burn victims.

2. Information Disclosure Statement

Chronic wounds are a potentially major complication for many people with complicating health factors because an inability to effectively synthesize collagen slows or prohibits the healing process and a suppressed immune system renders the individual susceptible to infection.

For example, it has been shown that a lack of insulin inhibits the healing process in diabetics by decreasing wound capillaries, fibroblasts, polymorphonuclear leukocytes, and collagen at the wound site. Additionally, platelets demonstrate an increase in aggregation, which inhibits their action. Platelets are a source of platelet-derived growth factors (PDGF) which enhance healing therefore any lack or malfunction of the platelets and subsequently of PDGF would have an adverse effect on healing.

Wounds can become a major complication in cancer patients if microbes invade the wound site because chemotherapy suppresses the immune system. Almost all chemotherapy agents currently available kill cancer cells by affecting DNA synthesis. For example, cyclophosphamide is an alkylating agent that is used in the treatment of chronic leukemias. Alkylating agents kill cancer cells by directly attacking DNA. However, in the process of attacking cancer cells, the alkylating agents also affect healthy cells and organs, including white blood cells and platelets thereby suppressing the patient's immune system.

Additionally, diabetics and patients with other metabolic disorders have an increased susceptibility to infection due to immune system abnormalities. Specifically, diabetics have deficiencies in white cell diapedesis, adherence, and chemotaxis. Hyperglycemia causes defective white cell phagocytosis and promotes growth of bacteria. Angiopathy, which leads to hypoxia, inhibits white blood cell (WBC) killing of bacteria by reducing the formation of superoxide radicals and impairs the delivery of antibiotics, antibodies, and granulocytes to the affected site.

Generally, bandages, creams, topical antibiotics, and mechanical scraping have been used as a first line of defense to treat chronic wounds. The surface of the wound is typically cleansed and/or sterilized to enhance the body's natural healing processes. However, these methods may be inadequate when natural healing mechanisms are affected by complicating factors such as chemotherapy which suppresses the immune system or diabetes which inhibits the production of collagen and/or fibroblasts at the wound site.

Thus a device and method is needed to accelerate wound healing that can effectively increase wound capillaries, fibroblasts, and collagen in the wound site, while simultaneously eliminating the risk of infection.

Ablative laser skin resurfacing (LSR) has been used to induce dermal collagen shrinkage to treat facial rhytides, acne scarring, and other blemishes by ablating or vaporizing skin in very thin layers, with a high level of control and without affecting the deep layers of the dermis. However, this method would not be advantageous for wound healing because ablative methods are often accompanied by complications such as persistent erythema, hyperpigmentation, hypopigmentation, scarring and infection.

Non-ablative laser skin resurfacing methods eliminate the complications commonly associated with ablative laser skin resurfacing by inciting a healing response in the dermis without damaging the epidermal barrier. The risk of infection and scarring is typically eliminated and erythema is greatly reduced when treating facial rhytides because the epidermal barrier remains intact. However in wound treatment, the epidermis may be damaged prior to laser therapy, therefore, the current non-ablative skin resurfacing methods do not provide a method to prevent infection in wound therapy which is essential in cases where complicating factors are present. Additionally, non-ablative skin resurfacing methods have found a need and benefit from employing a cooling mechanism to protect the epidermis. However, excess cooling can lead to fiber damage and a high radiant exposure is required for effective treatment.

Thus, a device and method is needed that can accelerate and improve the healing process, particularly in situations where complicating factors are present, without the complications associated with the prior art.

OBJECTS AND SUMMARY OF THE PRESENT INVENTION

It is an object of the present invention to provide a non-ablative laser system and method that will accelerate and improve the healing process without the complications associated with the prior art.

It is another aim of the present invention to employ a diode laser system to stimulate the healing process.

It is a further aim of the present invention to employ a wound cover that is transparent to a laser's radiation to protect the wound from thermal damage and to prevent infection.

It is an even further aim of the present invention to provide a method for wound healing that incorporates pre-radiation and post-radiation treatments, in addition to the laser therapy to further enhance the healing process.

Briefly stated, the present invention provides a non-ablative laser system and method that will accelerate and improve wound healing, particularly in situations where complicating factors are present. In particular, it is believed that the present invention produces selective papillary dermal injury which activates the production of fibroblasts and stimulates the synthesis of collagen to promote wound healing. Additionally, the likelihood of infection at the wound site is significantly reduced by simultaneously employing a transparent wound cover that allows for small molecule permeation, while effectively preventing microbial invasion. To further enhance the healing process, the laser therapy can be preceded by mechanically scraping the surface of the wound to remove necrotic tissue. Additional methods may also be employed after the laser treatment to prevent tissue dehydration, to accelerate angiogenesis, and to increase the breakdown of dead tissue and fibrin.

The above and other objects, features, and advantages of the present invention will become apparent from the following detailed description read in conjunction with the accompanying drawings.

DETAILED DESCRIPTION OF PREFERRED EMBODIMENTS

The present invention describes a new device and method for improving and accelerating the healing process of wounds particularly where complicating factors are present. A preferred embodiment of the present invention employs a 980 nm diode laser to produce selective papillary dermal injury which results in fibroblast activation and collagen synthesis at the wound site. Additionally, the 980 nm diode laser is capable of eradicating bacteria within the dermal region to significantly reduce the risk of infection, particularly in situations where the immune system is suppressed.

Figure 1:
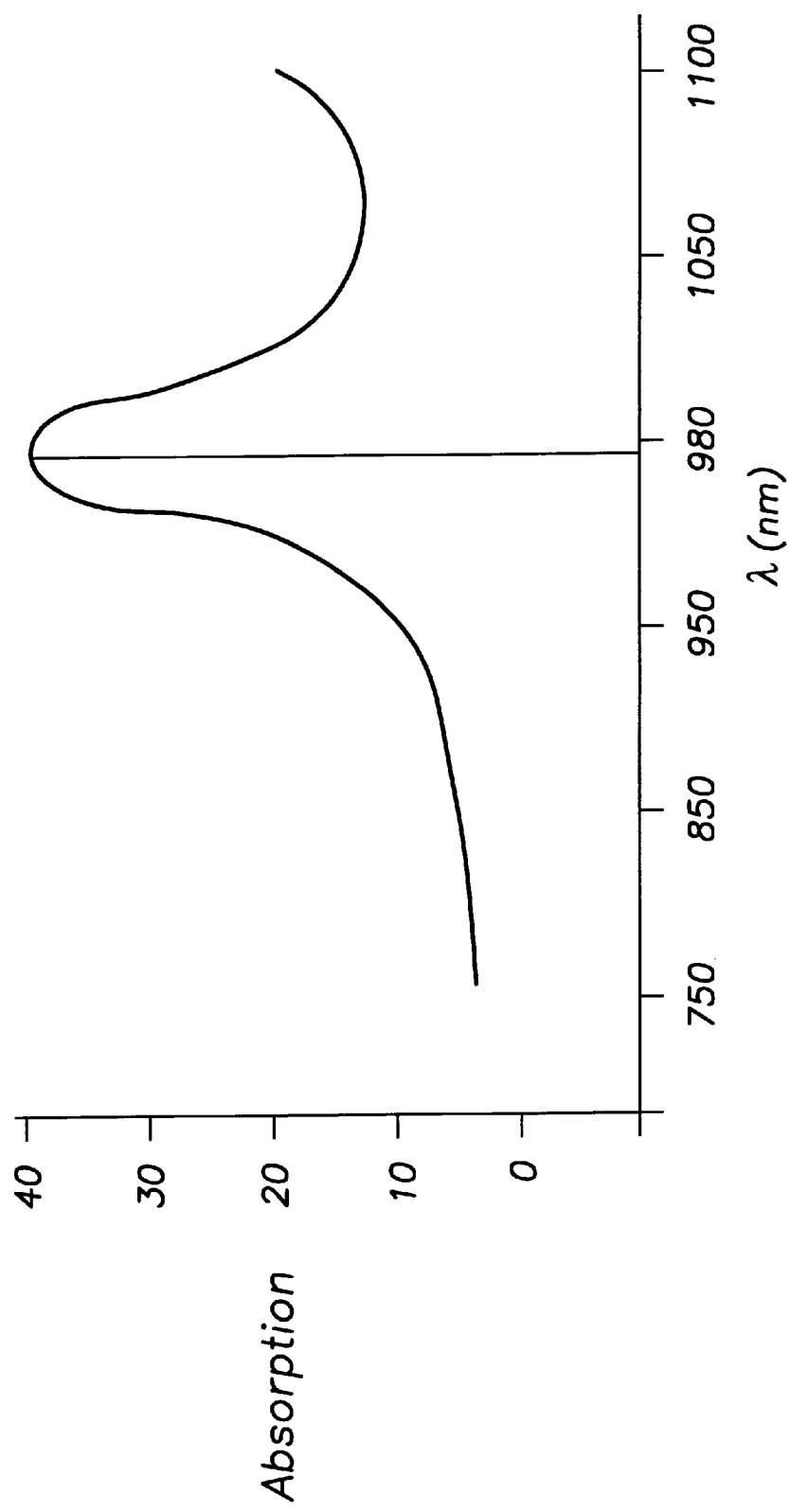
FIG. 1 Graph depicting $H_2O$ absorption spectra in wavelength of interest.

In FIG. 1, the absorption spectra of water illustrates a peak in the vicinity of 980 nm indicating that 980 nm light is well absorbed by water. The absorption spectra exhibits a valley in the 1064 nm range indicating that only moderate absorption can be achieved by lasers employing 1064 nm light. Thus, 980 nm radiation is preferred over 1064 nm for medical procedures involving soft tissue because greater absorption leads to high precision, low penetration results which is especially advantageous in the treatment of chronic wounds. Whereas, poorly absorbed wavelengths such as 1064 nm are transmitted through the tissue and penetrate deep into the dermis producing unwanted results for treating chronic wounds. Additionally, wavelengths such as 10 $\mu$m ($CO_2$), 3 $\mu$m (Ebrium YAG) or 2 $\mu$m (HoYag), which have even higher absorption coefficients than 980 nm, are counter productive for wound treatment. The upper layer can very easily vaporize or burn before the deeper layers are sufficiently heated because the laser radiation does not penetrate to the deeper layers. Thus, the 980 nm laser is preferred to selectively injure the lower papillary/upper reticular dermis to activate the synthesis of collagen and to eradicate bacteria within the dermis to accelerate and enhance the healing process. Additionally, visible 632 nm light can be used to irradiate the wound surface because 632 nm light has been proposed to stimulate and correct other metabolic processes on the cellular level.

It is known through research in the area of laser skin resurfacing that high radiant exposures are required to stimulate the healing process when treating facial rhytides. For example, treating facial rhytides with 1.32 $\mu$m wavelength laser light delivered through a fiberoptic handpiece into a 5 mm diameter spot using 20 ms duration pulses and pulse radiant exposures ranging from 26–29 $J/cm^2$ will only achieve mild wrinkle reduction. Significantly higher laser radiant exposures are required to stimulate the healing process to achieve effective reduction of facial rhytides.

Whereas, the present invention is capable of stimulating the healing process at significantly lower radiant exposures. The present invention typically employs 15–25 W of power to irradiate a wound site. Additionally, 400–600 $\mu$m optical fibers are used to radiate the wound's surface from a distance of several millimeters. The fibers and/or the radiation spot may be manually moved over the surface of the wound or a scanner may be employed to evenly irradiate the wound site.

Figure 2:
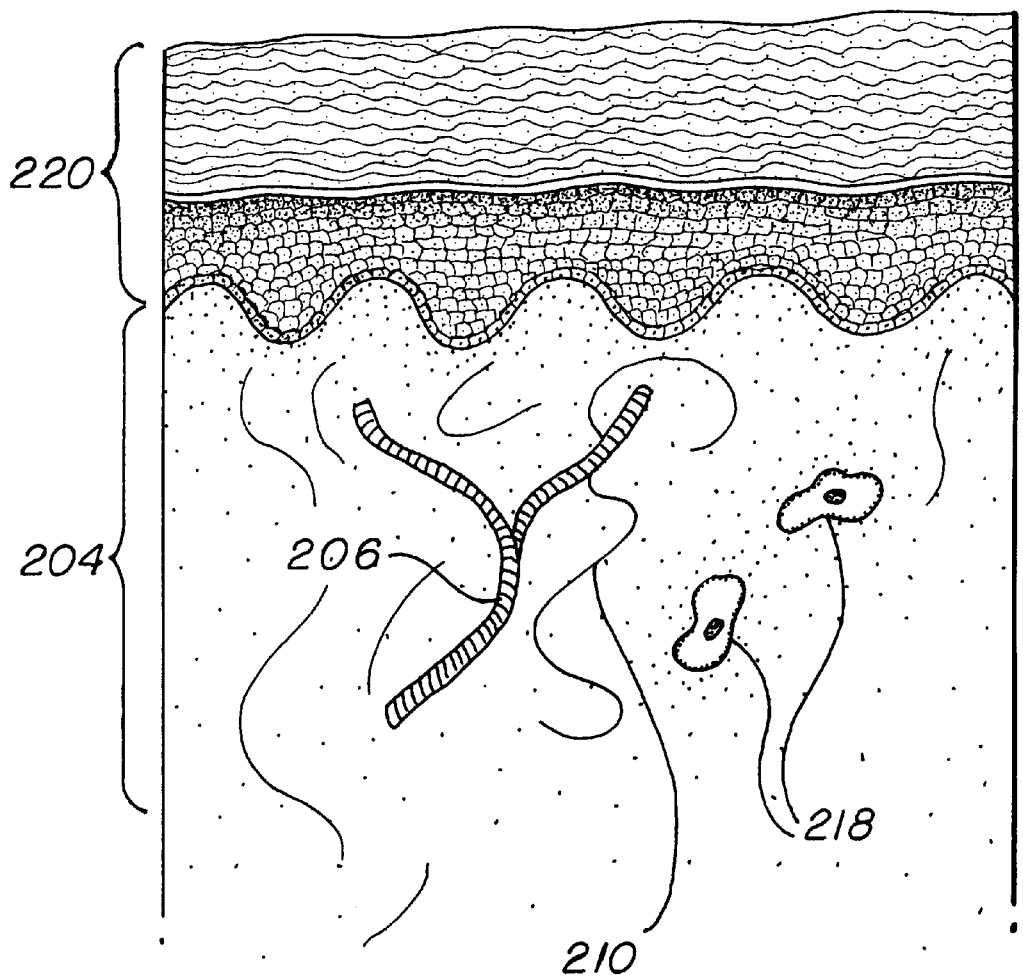
FIG. 2 Cross-section of tissue to show effect of laser irradiation.
Figure 3:
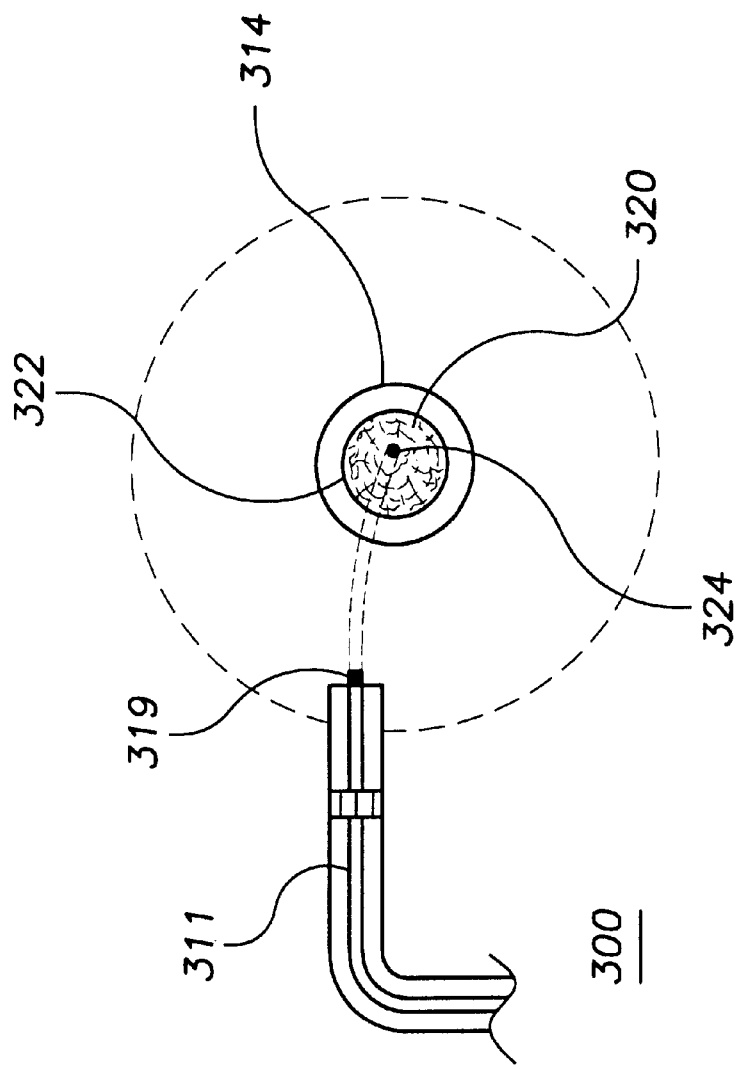
FIG. 3 Schematic view of laser system employed on diabetic foot ulcer.

FIGS. 2 and 3 illustrate a specific example and preferred embodiment of the present invention in which 980 nm diode laser system 300, operating at only 15 W, was employed to selectively heat collagen fibrils 206 in subsurface layers 204 to treat approximately a 108 $cm^2$ diabetic foot ulcer as wound site 314.

Foot ulcers are a potentially serious complication for diabetics because the healing process is inhibited by a decrease in wound capillaries, fibroblasts, and collagen at the wound site and by immune system abnormalities which impair the immune system's ability to effectively fight infection. The present invention activates the synthesis of collagen and the production of wound fibroblasts at the wound site and eradicates bacteria in the dermis to accelerate the healing process.

In the present example, the radiation was delivered to wound site 314 in a continuous mode by optical fibers 311 made of plastic clad silica (PCS) having a numerical aperture of 0.33. Additionally, laser device 300 employing aiming beam 319 simultaneously delivered visible and invisible light to wound site 314. The surface of wound site 314 was scanned in a spiral pattern 320 that started from rim 322 and converged to center 324 was employed to increase absorption selectivity until a change in color was observed (approximately 240 seconds). Irradiation was then applied to the perimeter to increase the temperature of the surrounding tissue.

It is thought that the laser's radiation produced selective absorption at lower papillary/upper reticular region 210 which subsequently activated the papillary dermal fibroblasts to synthesize procollagen I, the synthetic precursor to collagen I. A temperature increase applied over a period of several milliseconds caused the phase transition of procollagen I to collagen I within the papillary dermis and superficial reticular dermis. Additionally, the collagen thermal modification was probably sufficient to activate the fibroblasts to produce a long-term healing response.

The appearance of wound fibroblasts 218 resulted in wound contraction and tightening of the overlying epidermis 220. Specifically, it is thought that the multipotential fibroblasts undergo a metamorphosis to myofibroblasts assuming some of the characteristics of smooth muscle cells. The actin filaments of the myofibroblasts exert a traction force upon the collagneous matrix thereby causing the granulation tissue to contract. Additionally, cell-cell adhesions and cell-fibronectin linkages may have provided additional means by which the traction forces of the myofibroblast may be transmitted across the wound matrix to achieve wound contraction and a tightening of the overlying epidermis.

Additionally, it is believed that the present laser device is capable of eradicating bacteria within the dermis to significantly reduce the risk of infection. Experiments conducted at the University of Glasgow by Ian Watson and Duncan Stewart-Tull (Photonics Spectra Vol. 32, February 1998) are indicating that laser radiation has a far more destructive effect on bacteria than would be expected from mere thermal considerations. For instance, when *E. coli* suspensions are heated in a waterbath to 50° C. and left for 20 minutes, bacteria viability dropped by one D-value (90 percent). Whereas, exposure to light from a 100-W Nd:YAG laser raised the temperature to 50° C. in 25 seconds and dropped the *E. coli* viability by three D-values (99.9 percent). The bacterial cells blistered and there was evidence of cell rupture. Thus a similar destructive effect on bacteria in the wound site can be assumed to contribute to the remarkable success of the present invention. Eradication of bacteria in the dermis is especially advantageous for treating wounds particularly in situations where the immune system is suppressed.

Figure 4:
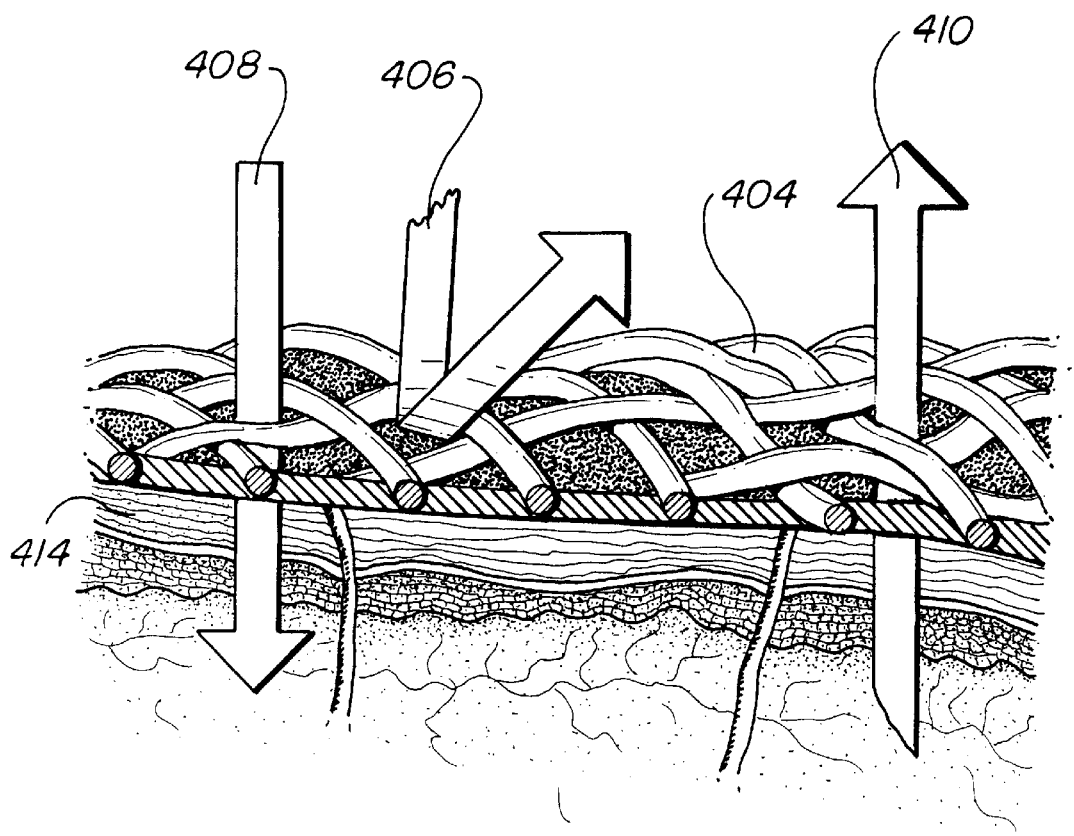
FIG. 4 Schematic view of wound cover.

FIG. 4 shows another specific embodiment of the present invention, in which wound site 414 is protected from microbial invasion by special wound cover 404 (commercially available as Amino-Plex or Omiderm). The pore structure of wound cover 404 allows oxygen and aqueous medications 408 to permeate in and moisture 410 to escape from the surface of wound site 414, while simultaneously preventing the invasion of microbes 406. Wound cover 404 is transparent to the laser's radiation and therefore can be applied prior to the laser therapy. A laser system applies 980 nm radiation to eradicate bacteria deep within the tissue, while wound cover 404 prevents microbes 402 from invading wound site 414 after laser therapy. Typically a penetration depth of 1 mm is preferred to obtain optimal sterilization effects. Wound cover 404 is preferred over other types of bandages because wound cover 404 is applied prior to laser therapy and does not need to be changed or removed until wound site 414 has healed. In contrast, bandages that can only be applied after laser therapy, because they are not transparent to the laser's radiation, increase the probability of microbial invasion because the wound is exposed immediately following laser therapy. Additionally, airtight bandages that prevent microbial invasion prohibit moisture from escaping thereby allowing bacteria, present at the time of the procedure, to flourish under the bandage. Alternatively, if the bandage allows the moisture to escape, then microbial invasion is likely to occur through the same openings that enabled the moisture to escape. Thus, to obtain optimal results special wound cover 404 should be transparent and should allow for small molecule permeation, while effectively preventing microbial invasion.

As depicted in the previous example, particular pre-treatment methods can be especially advantageous in wound healing when used in conjunction with the present laser device. For example, laser therapy can be preceded by mechanically scraping the surface of the wound. Mechanical scraping removes necrotic tissue and debris from the wound surface to prepare the wound site for laser therapy. A transparent wound cover with a bacteriostatic or bactericidal agent can then be applied to the wound site to prevent microbial invasion and to allow moisture to escape from the wound surface. The photothermal energy selectively stimulates the lower papillary/upper reticular dermis which leads to fibroblast activation and synthesis of new collagen and extracellular matrix material. To further enhance the healing process, additional methods may be employed after the laser treatment to accelerate angiogenesis, and to increase the breakdown of dead tissue and fibrin.

Having described preferred embodiments of the invention with reference to the accompanying drawings, it is to be understood that the invention is not limited to these precise embodiments, and that various changes and modifications may be effected therein by one skilled in the art without departing from the scope or spirit of the invention as defined in the appended claims.

What is claimed is:

1. A treatment method for healing wounds, using a non-ablative laser system, comprising the steps of:

positioning a non-ablative laser having an operating wavelength of about 980 nm, which is absorbed by tissue and which penetrates a wound site;

connecting with said laser, means to transport laser radiation to said wound site; and irradiating said wound site with said non-ablative laser radiation at a power of about 5 watts, wherein said laser radiation is continuously applied for a preselected time, which is between about 10 seconds and about 20 minutes.

2. A treatment method according to claim 1 wherein said wound site is scanned in a spiral pattern, starting at a rim and converging to a center.

3. A treatment method according to claim 2 where said laser is scanned around the periphery of said wound site.

4. A treatment method according to claim 3 further comprising a step of:

applying a wound cover that is transparent to said laser radiation prior to said laser treatment and that allows for permeation of small molecules, while simultaneously preventing microbial invasion.

5. A treatment method according to claim 4 further comprising a pre-treatment step of:

scraping said wound site in preparation for said laser treatment.

6. A treatment method according to claim 1 further comprising a pre-treatment step of:

scraping said wound site in preparation for said laser treatment.

7. A treatment method according to claim 6 further comprising a post-treatment step of:

rewetting said wound site following said laser radiation.

8. A treatment method according to claim 1 where a post-treatment step is used in conjunction with a pretreatment step.

9. A treatment method according to claim 1 further comprising a step of:

applying a wound cover that is transparent to said laser radiation prior to said laser treatment and that allows for permeation of small molecules, while simultaneously preventing microbial invasion.

10. A treatment method according to claim 9 further comprising a pre-treatment step of:

scraping said wound site in preparation for said laser treatment.

* * * * *